United States Patent [19]

Lyons

[11] Patent Number: 5,152,799
[45] Date of Patent: Oct. 6, 1992

[54] PROSTHETIC FEMORAL STEM

[75] Inventor: Matthew Lyons, West Brookfield, Mass.

[73] Assignee: Exactech, Inc., Gainesville, Fla.

[21] Appl. No.: 771,773

[22] Filed: Oct. 4, 1991

[51] Int. Cl.⁵ .............................. A61F 2/36; A61F 2/28
[52] U.S. Cl. ........................................ 623/23; 623/16
[58] Field of Search ................. 623/23, 22, 18, 16

[56] References Cited

U.S. PATENT DOCUMENTS

| | | | |
|---|---|---|---|
| 4,404,693 | 9/1983 | Zweymuller | 623/23 |
| 4,714,470 | 12/1987 | Webb, Jr. et al. | 623/23 X |
| 4,908,035 | 3/1990 | Deckner et al. | 623/23 |
| 5,004,475 | 4/1991 | Vermeire | 623/23 |

OTHER PUBLICATIONS

Englehardt, J. A. et al., "Hip Stem Fixation and Tip Geometry: A Theoretical Model for Thigh Pain", Mar. 4-7, 1991, 37th Ann. Orthopedic Research Society.

Primary Examiner—Ronald Frinks
Attorney, Agent, or Firm—Spensley Horn Jubas & Lubitz

[57] ABSTRACT

A femoral stem prosthesis including a stem tapering from a proximal end to a distal end, and having a primary zone of taper and a secondary zone of taper. The secondary zone of taper, located at the distal end of the stem, has a larger angle of taper than that of the primary zone of taper, but substantially less than the taper in prior art stems. In the secondary zone of taper, the stem gradually tapers away from the femoral bone to avoid a sudden change in stress level in the bone at the distal stem tip, thus avoiding the incidence of thigh pain. The stem of the inventive prosthesis preferably includes longitudinal channels to increase its flexibility and preferably has a trapezoidal cross-sectional geometry to resist rotational forces and to provide multi-plane stability within the femur, thereby providing effective stress transfer to the femur.

15 Claims, 2 Drawing Sheets

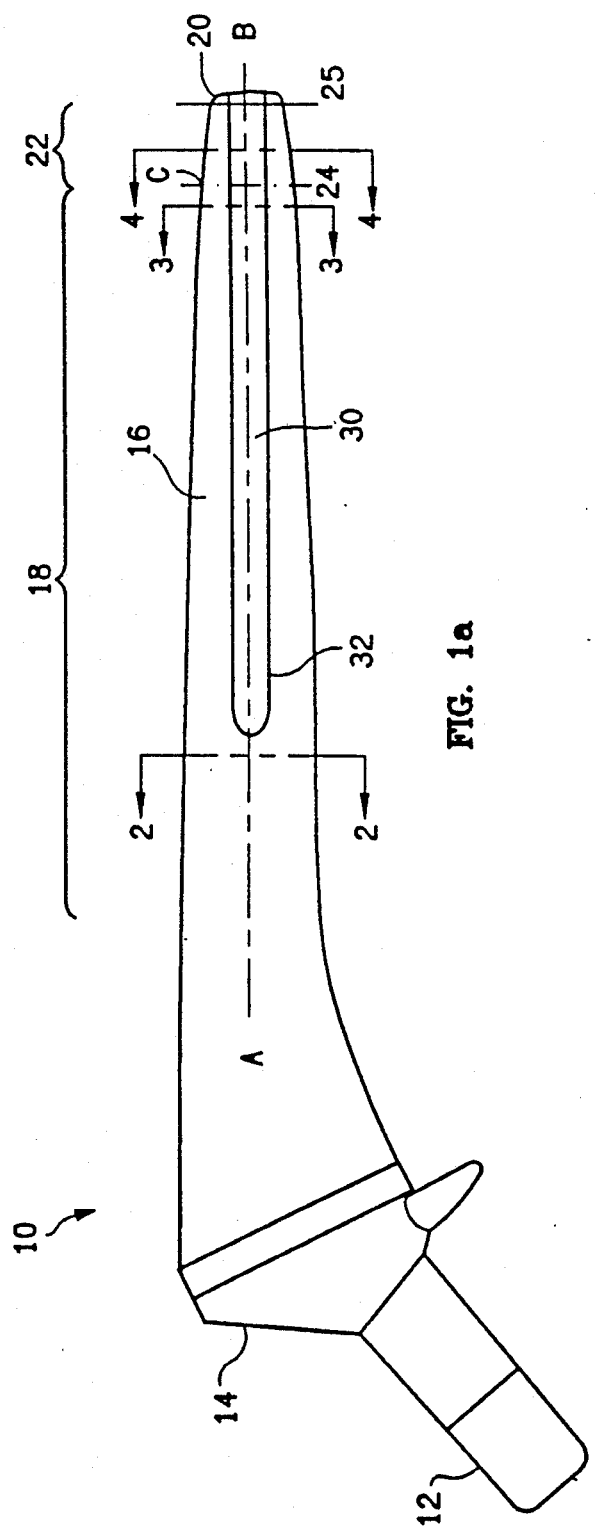
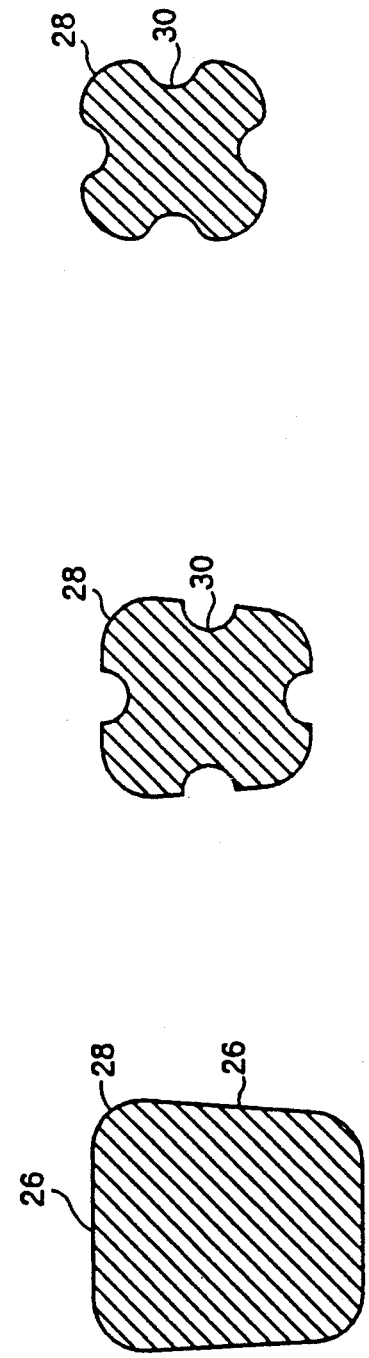
FIG. 1a
FIG. 2
FIG. 3
FIG. 4

PROSTHETIC FEMORAL STEM

BACKGROUND OF THE INVENTION

1. Field of the Invention

The present invention relates generally to cementless total hip arthroplasty and, more particularly, to an improved press-fit femoral stem prosthesis.

2. Related Art

In recent years, cementless total hip arthroplasty has enjoyed significant clinical success. To date, the design of press-fit femoral stem prostheses has focused on providing a tight fit within the metaphyseal portion of the femur to eliminate the potential for relative motion. Prior art femoral stem prostheses generally have a circular or rectangular cross-sectional shape and end abruptly in a blunt tip distally. While some of the prior art femoral stem prostheses have achieved the desired tight fit, two major problems remain associated with press-fit stems: the occurrence of thigh pain and abnormal femoral bone remodeling.

It is now believed that the thigh pain and femoral bone remodeling which occur with prior art press-fit femoral stem prostheses result from stem stiffness and the concentration of bending stress at the distal tip of the implants. Since bone tissue will remodel in direct relation to the stress applied to it, it is desirable to equalize the application of stress over the length of the femur following implantation of the prosthesis to avoid bone resorption in some areas and hypertrophy in other areas. Unfortunately, due to their mechanical stiffness, prior art femoral stem prostheses stress-shield the proximal end of the femur, leading to bone resorption in this region. Stress transfer occurs primarily at the prosthesis/bone interface at the blunt distal end of prior art prosthetic stem designs, leading to bone hypertrophy in this region.

It is an object of the present invention to eliminate the thigh pain and to decrease the bone remodeling which occur with other press-fit stems.

SUMMARY OF THE INVENTION

The femoral stem prothesis of the present invention provides multi-plane stability within the femur while substantially eliminating thigh pain. The invention minimizes femoral bone remodeling by providing increased stress transfer in the mid and proximal regions of the prosthesis and by minimizing stress transfer in the distal stem area.

The inventive prothesis includes a neck and a stem, the stem being designed to be embedded in the femur of a patient. The stem has a gradual proximal to distal end taper to conform to the geometry of the metaphyseal portion of the femur. Significantly, at its distal end, the stem includes a secondary zone of taper wherein the stem gradually tapers away from the bone. A sudden change in stess level in the bone at the distal stem tip and the accompanying incidence of thigh pain is thus avoided.

In the preferred embodiment of the invention, the stem has a trapezoidal cross-sectional geometry to provide a tight fit within the metaphyseal portion of the femur and to resist rotational forces. The tight fit of the inventive femoral stem prosthesis, in turn, provides effective stress transfer to the femur and maximum resistance to rotational forces.

The inventive prosthesis is preferably composed of a biocompatible material. In the preferred embodiment, the stem of the inventive prosthesis is made of a titanium alloy to increase stem flexibility and decrease stress-shielding of the femur. Additionally, the stem of the preferred embodiment is provided with a plurality of longitudinal channels to further reduce its stiffness.

Additional features and advantages of the invention will become apparent from the following detailed description read in conjunction with the following drawings.

BRIEF DESCRIPTION OF THE DRAWINGS

FIG. 1*a* is a side view of the preferred embodiment of the inventive prosthetic stem.

FIG. 2 is a cross-sectional view of FIG. 1 taken along lines 2—2.

FIG. 3 is a cross-sectional view of FIG. 1 taken along lines 3—3.

FIG. 4 is a cross-sectional view of FIG. 1 taken along lines 4—4.

Like numerals in the drawings refer to like parts.

DETAILED DESCRIPTION OF THE PREFERRED EMBODIMENT

The following description is of the best presently contemplated mode for carrying out the invention. This description is made for purpose of illustrating the general principles of the invention and should not be taken in a limiting sense. The scope of the invention is best determined by reference to the appended claims.

Figure 1B:
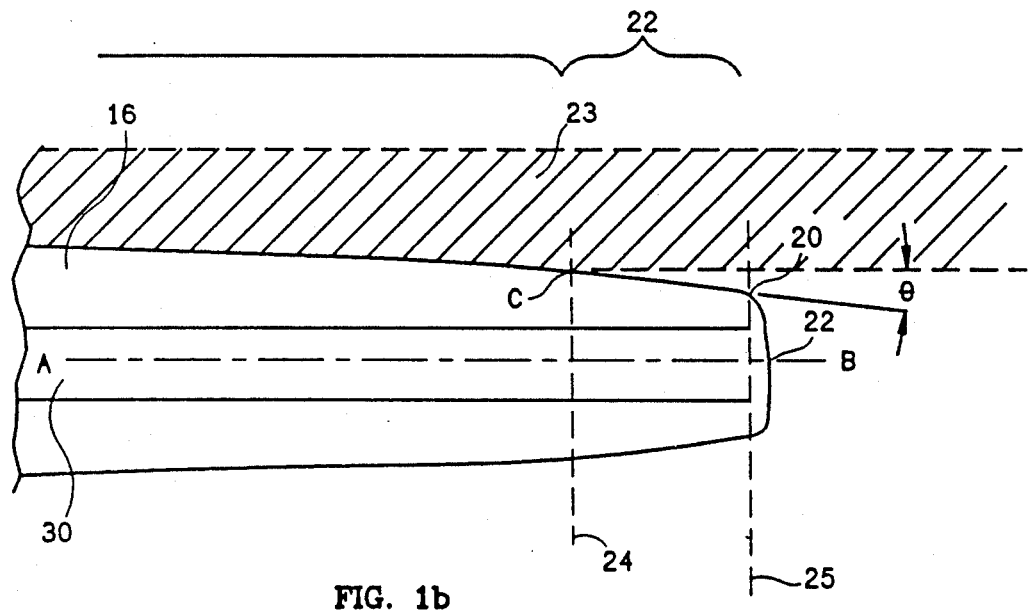
FIG. 1*b* is an enlarged side view of the distal end of FIG. 1*a*.

FIG. 1*a* depicts a side view of the preferred embodiment of the inventive femoral stem prosthesis 10. The prosthesis 10 includes a neck 12, a collar 14, and a stem 16. The neck 12, collar 14 and stem 16 are preferably made of a titanium alloy to provide maximum compatibility with the femoral bone and to maximize stem strength and flexibility. However, other biocompatible materials, e.g., ceramics, composites or other metal alloys, having the requisite strength and flexibility may be used. Furthermore, while the preferred embodiment of the invention includes a collar, the invention encompasses collarless prostheses.

Figure 1C:
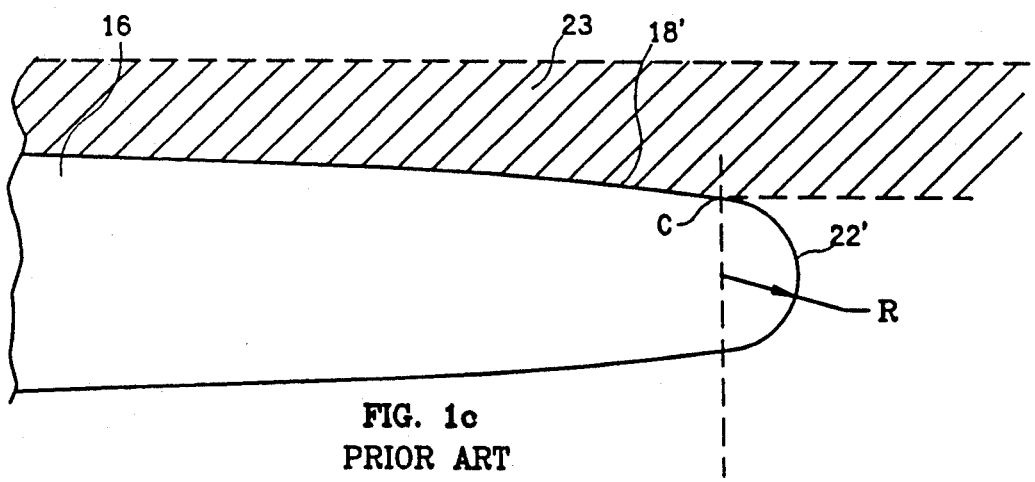
FIG. 1*c* is an enlarged side view of the distal end of a prior art prosthetic stem.

Stem 16 is provided with a gradual proximal to distal end taper. This taper includes a primary zone of taper 18 having an angle of taper ranging from approximately 1° to 2° per side (measured from a center line A-B) preferably approximately 1.5°, designed to conform to the narrowing of the metaphyseal portion of the femur. In accordance with the present invention, to avoid a sudden change in stress level in the femur at the blunt distal end 20 of the prosthetic stem 16, the distal portion of stem 16 is provided with a secondary zone of taper 22, shown englarged in FIG. 1*b*. In the secondary zone of taper 22, the stem 16 gradually tapers away from the femoral bone 23 (shown in dotted outline on one side only of the stem 16). The secondary zone of taper 22 has an angle of taper Θ ranging from approximately 2° to 4° per side, with respect to the primary zone of taper 18, with larger taper angles for larger, and consequently stiffer, prostheses. Preferably, the angle of taper of the secondary zone of taper 22 is approximately 1° greater per side than the angle of taper of the primary zone of taper 18. That is, if the primary zone taper is 1.5°, then preferably the secondary zone taper is an additional 1°, or 2.5° with respect to the center line A-B. The present invention thus differs from the prior art, shown enlarged in FIG. 1c, which has a first taper 18' that directly transitions to a blunt distal end 22', which results in a sharper transition from the surface of the bone 23.

The radius of curvature between the primary zone of taper 18 and the secondary zone of taper 22 at point C ranges from approximately 0.75 to 2.0 inches, being preferably approximately 1.0 inch. The transition from the primary zone 18 to the secondary zone 22 occurs at a point 24 located approximately 90% down the stem 16 (approximately 0.5 inch from the distal end 20 in smaller sizes of prostheses to approximately 0.75 inch from distal end 20 in larger sizes). This again contrasts with the prior art shown in FIG. 1c, in which the equivalent transition point C has a radius of curvature R of about one-half the diameter of the stem 16 at its distal end 22'. In the present invention, the secondary zone 22 transitions to the blunt distal end 20 at a point 25, at which point the stem 16 does not contact the bone 23.

It has been found that the tapered stem design, including the secondary zone of taper 22, provides increased proximal stress transfer and minimizes stress transfer at the distal end 20 of stem 16. The occurrence of thigh pain can thus be substantially eliminated.

In the preferred embodiment of the invention, as shown in FIGS. 1a and 2-4, the stem 16 has a trapezoidal cross-sectional geometry including four substantially flat faces 26 and four beveled edges 28. It has been determined that the trapezoidal cross-sectional geometry of the stem provides excellent proximal fill of the metaphyseal portion of the femur for optimum stress transfer to the femur. Additionally, this cross-sectional geometry provides maximum resistance to rotational forces.

The stem 16 of the preferred embodiment of the present invention is provided with a longitudinal channel 30 in each face 26. The channels 30, preferably extend along at least the distal half of the stem and more preferably along approximately 55% of the stem length. (The length of the channels ranges from approximately 3 to 4 inches, depending on the size of the prosthesis 10.) The depth of the channels 30 ranges from approximately 0.05 to 0.15 inch, while the diameter of the channels 30 ranges from approximately 0.10 to 0.30 inch, depending on the size of the prosthesis 10. The channels 30 yield an increase in flexibility of the stem 16 of approximately 5-20% compared to non-channeled stems (preferably 16-19% in larger sized prostheses), thereby reducing the distal stem stress transfer.

To reduce stress concentration (caused by bending) at the channel run-out 32, the channel exit radius of curvature is preferably approximately 1.5 to 2.5 inches. However, other radii of curvature may be used, provided the transition from channeled to nonchanneled stem is gentle.

The presence of channels 30 is particularly desirable in large size femoral stem prostheses, the stiffness of which would otherwise lead to significant stress-shielding of the femur with resulting bone resorption. In smaller size stem prostheses made of a flexible material like a titanium alloy, provision of channels 30 may not be necessary since the stem material alone provides the desired flexibility.

One preferred embodiment of the present invention has been illustrated and described. Nevertheless, it will be understood that various modifications may be made without departing from the spirit and scope of the invention. For example, in certain cases it may be desirable for the stem to have an oval or rectangular cross-sectional geometry. Also, as previously mentioned, the prostheses need not include a collar. Accordingly, it is to be understood that the invention is not to be limited by the specific illustrated embodiment, but only by the scope of the appended claims.

I claim:
1. A femoral stem prosthesis comprising:
   a. a neck, and
   b. a straight stem dimensioned to fill the metaphyseal portion of a femur upon implantation therein, the stem having four sides and tapering from a proximal end to a blunt distal end, the taper of the stem including a primary zone of taper having a first angle of taper, ranging from approximately 1° to 2° per side measured from the stem's longitudinal centerline, and a secondary zone of taper located distally of the primary zone of taper and proximally of the blunt distal end, and having a second angle of taper, the second angle of taper ranging from approximately 2° to 4° per side measured from the stem's longitudinal centerline, wherein the secondary zone of taper tapers away from the femoral bone.

2. The femoral stem prosthesis of claim 1, wherein the second angle of taper is approximately 1° larger per side than the first angle of taper.

3. The femoral stem prosthesis of claim 1, wherein a radius of curvature between the primary zone of taper and the secondary zone of taper ranges from approximately 0.75 to 2.0 inches 4. The femoral stem prosthesis of claim 3, wherein the radius of curvature between the primary zone of taper and the secondary zone of taper is approximately 1.0 inch.

5. The femoral stem prosthesis of claim 1, wherein approximately 90% of the length of the stem is located proximal of the secondary zone of taper.

6. The femoral stem prosthesis of claim 1, wherein the secondary zone of taper begins approximately 0.5 to 0.75 inches from the distal end of the stem.

7. The femoral stem prosthesis of claim 1, wherein the stem has a trapezoidal cross-sectional geometry including four faces and four longitudinal edges.

8. The femoral stem prosthesis of claim 7, wherein the longitudinal edges of the stem are beveled.

9. The femoral stem prosthesis of claim 7, wherein the stem is provided with at least one longitudinal channel.

10. The femoral stem prosthesis of claim 9, wherein the stem is provided with one longitudinal channel in each face.

11. The femoral stem prosthesis of claim 10, wherein the channels extend along at least the distal half of the stem.

12. The femoral stem prosthesis of claim 1, further comprising a collar.

13. The femoral stem prosthesis of claim 1, wherein the neck and the stem are composed of a biocompatible material.

14. The femoral stem prosthesis of claim 13, wherein the biocompatible material is a metal alloy.

15. The femoral stem prosthesis of claim 14, wherein the metal alloy is a titanium alloy.

* * * * *